United States Patent [19]
Johnson

[11] Patent Number: 6,107,061
[45] Date of Patent: Aug. 22, 2000

[54] MODIFIED PRIMER EXTENSION REACTIONS FOR POLYNUCLEOTIDE SEQUENCE DETECTION

[75] Inventor: Martin D. Johnson, Woodside, Calif.

[73] Assignee: The Perkin-Elmer Corporation, Foster City, Calif.

[21] Appl. No.: 09/399,501

[22] Filed: Sep. 18, 1999

[51] Int. Cl.⁷ ........................................ C12P 19/34
[52] U.S. Cl. .............................. 435/91.1; 435/6; 435/183; 435/810; 436/172; 536/22.1; 536/24.3; 536/24.33; 536/25.3
[58] Field of Search ................................ 435/6, 91.1, 183, 435/810; 436/94, 800, 172; 536/22.1, 24.3, 24.33, 25.3

[56] References Cited

U.S. PATENT DOCUMENTS

| | | | |
|---|---|---|---|
| 5,625,081 | 4/1997 | Trainor | 549/392 |
| 5,925,520 | 7/1999 | Tully et al. | 435/6 |

FOREIGN PATENT DOCUMENTS

9840496  9/1998  WIPO .

*Primary Examiner*—Bradley L. Sisson
*Attorney, Agent, or Firm*—Scott R. Bortner

[57] ABSTRACT

The present invention relates to assays for the detection of nucleotide bases at predetermined locations on polynucleotides of interest. The embodiments of the invention include techniques relating to methods in which a primer extension reaction is designed to only extend a single nucleotide base. The invention, in part, relates to the improvement of adding corresponding non-labeled chain terminators to a primer extension reaction so as to increase the accuracy and reliability of nucleotide base determinations made by the assay. The invention is particularly useful when applied to assay methods in which the primer extension reaction is detected by a fluorescent dyes conjugated to chain terminators incorporated in the extension reactions. A first embodiment of the invention relates to methods for identifying a nucleotide base at the predetermined location on a polynucleotide of interest. Other embodiments of the invention include compositions for identifying a nucleotide base at a predetermined location on a polynucleotide of interest. One embodiment of such a composition is a mixture comprising a polynucleotide for analysis, an extendable polynucleotide that can hybridize of a specific location on the polynucleotide for analysis, a first labeled terminator, a second labeled terminator, and an unlabeled terminator corresponding of the first labeled terminator. The compositions may comprise additional labeled terminators and corresponding unlabeled terminators. Another embodiment of the subject compositions is a mixture comprising at least two labeled terminators and one or more corresponding unlabeled terminators. The compositions may comprise additional labeled terminators and corresponding unlabeled terminators. Other embodiments of the invention include kits for identifying a nucleotide base at a predetermined location on the polynucleotide of interest.

23 Claims, No Drawings

MODIFIED PRIMER EXTENSION REACTIONS FOR POLYNUCLEOTIDE SEQUENCE DETECTION

FIELD OF THE INVENTION

This invention is in the field of polynucleotide base sequence determination.

BACKGROUND

Techniques for the analysis of nucleic acid sequences have found widespread use in basic research, diagnostics, and forensics.

DNA sequencing techniques such as Sanger-Coulson chain terminator sequencing and Maxim and Gilbert sequencing have been used to determine the nucleotide base sequences of large polynucleotides. In many instances, it is of interest to use a simplified technique in order to obtain nucleic acid sequence information about short stretches, e.g., 1 base, of DNA than is typically obtained with sequencing techniques designed to obtain base sequences for comparatively longer regions (e.g., 50–800 bases).

Of particular interest is the use of primer extension techniques that result in the addition of a single nucleotide to the 3' end of polynucleotide probe, such as described in Syvanen et al, Genomics 8, 684–642 (1990). A common embodiment of primer extension analysis adapted for the identification of simple polynucleotides is often referred to as "mini-sequencing." Single base polynucleotide extension techniques such as mini-sequencing are typically used in a solid-phase format in which a binding moiety on the primer or the chain terminators becomes immobilized on a solid phase so as to provide for the detection of the incorporated terminator. The inventors have discovered that differences in the incorporation rate of different labeled polynucleotide chain terminators, can substantially reduce the accuracy and reliability of chain terminator extension. Primer extension techniques such as mini-sequencing employing a fluorescence detecting electrophoresis apparatus, e.g., an automated DNA sequencer, are particularly sensitive to differences in the incorporation rate, e.g., the inability to distinguish heterozygotes from nucleotide misincorporation. The invention described herein greatly reduces the problems associated with differential incorporation of labeled terminators.

SUMMARY

The present invention relates to assays for the detection of nucleotide bases at predetermined locations on polynucleotides of interest. The embodiments of the invention include techniques relating to methods in which a primer extension reaction is designed to only extend a single nucleotide base. The invention, in part, relates to the improvement of adding corresponding non-labeled chain terminators to a primer extension reaction so as to increase the accuracy and reliability of nucleotide base determinations made by the assay. The invention is particularly useful when applied to assay methods in which the primer extension reaction is detected by a fluorescent dyes conjugated to chain terminators incorporated in the extension reactions.

A first embodiment of the invention relates to methods for identifying a nucleotide base at the predetermined location on a polynucleotide of interest. The methods employ the step of extending an extendable polynucleotide, e.g., an oligonucleotide primer, by a single base. The extension takes place in a reaction mixture comprising (1) two or more labeled terminators, each terminator having a different nucleotide base and different detectable label, and (2) one or more corresponding unlabeled terminators, where the corresponding unlabeled terminators have a nucleotide base that is functionally identical to a nucleotide base on a labeled terminator in the reaction mixture. In a preferred embodiment of the invention, extension takes place in the presence of (1) four labeled terminators, each terminator having a different nucleotide base each having a different detectable label associated with the base (2) and three corresponding unlabeled terminators, each having a different nucleotide base that functionally corresponds to the nucleotide bases of the labeled terminators. The labeled terminators are preferably labeled with fluorescent dyes that are readily distinguished from one another, i.e., the dyes are spectrally resolvable.

Other embodiments of the invention include compositions for identifying a nucleotide base at a predetermined location on a polynucleotide of interest. The subject compositions include mixtures that are formed in the course of performing the methods of the invention or compositions that may be formed in the process of preparing to perform methods of the invention. One embodiment of such a composition is a mixture comprising a polynucleotide for analysis, an extendable polynucleotide that can hybridize of a specific location on the polynucleotide for analysis, a first labeled terminator, a second labeled terminator, and an unlabeled terminator corresponding of the first labeled terminator. The compositions may comprise additional labeled terminators and corresponding unlabeled terminators. Another embodiment of the subject compositions is a mixture comprising at least two labeled terminators and one or more corresponding unlabeled terminators. The compositions may comprise additional labeled terminators and corresponding unlabeled terminators.

Other embodiments of the invention include kits for identifying a nucleotide base at a predetermined location on the polynucleotide of interest. Embodiments of the subject kits include a plurality of reagents that may be used to perform nucleotide base identification in accordance with one or more methods of the invention. The kits contain a labeled terminator and a corresponding unlabeled terminator present in the same solution. The kits of the invention may also include additional labeled terminators and corresponding unlabeled terminators present in the same solution or in separate solutions. The kits may further comprise one or more of the following items, DNA polymerase, alkaline phosphates, chromatography columns, reaction buffers, instructions, and the like.

SPECIFIC EMBODIMENTS OF THE INVENTION

Definitions

"Terminator": refers to an enzymatically-incorporable nucleotide or nucleotide analog in which the sugar moiety does not support incorporation of subsequent nucleotides or nucleotide analogs. Typical terminators are those in which the nucleobase is a purine, a 7-deaza-purine, a pyrimidine, a normal nucleobase or a common analog thereof and the sugar moiety is a pentose which includes a 3'-substituent that blocks further synthesis, such as a ddNTP. Substituents that block further synthesis include, but are not limited to, amino, deoxy, halogen, alkoxy and aryloxy groups. Exemplary terminators include, but are not limited to, those in which the sugar-phosphate ester moiety is 3'-($C_1$–$C_6$)alkylribose-5'-triphosphate, 2'-deoxy-3'-($C_1$–$C_6$)alkylribose-5'- triphosphate, 2'-deoxy-3'-($C_1$–$C_6$)alkoxyribose-5-triphosphate, 2'-deoxy-3'-($C_5$–$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate.

"Labeled terminator" refers to a terminator that is physically joined to a detectable label. The linkage to the detectable label is at a site or sites on that terminator that do not prevent the incorporation of the terminator into a polynucleotide in a reaction catalyzed by a DNA polymerase. The detectable label serves to (1) signal the incorporation of the terminator into a polynucleotide and (2) to indicate the structure of the nucleotide base moiety of the terminator that has been incorporated by way of a predetermined correlation between the signal produced by the detectable label and the structure of the labeled terminator. Preferably, the detectable label is a fluorescent dye. Fluorescent dyes useful as detectable labels are well known to those skilled in the art and numerous examples can be found in the *Handbook of Fluoresdent Probes and Research Chemicals 6$^{th}$ Edition*, Richard Haugland, Molecular Probes, Inc., 1996 (ISBN 0-9652240-0-7). The detectable label may be joined directly to the terminator or may be joined through a linker. Examples of suitable linkers are described in U.S. Pat. No. 5,770,716. Preferably, and the detectable label is joined to the nucleotide base moiety of the terminator so as not to prevent the incorporation of the labeled terminator in a DNA polymerase catalyzed reaction. Detectable labels may be compounds or elements detectable by techniques other than, or in addition to, fluorescence. Such additional labels include radioisotopes, chemiluminescent compounds, spin labels, immunologically detectable haptens, and the like.

"Corresponding unlabeled terminator" refers to a terminator that does not comprise a detectable label that produces an interfering detectable signal and is defined with respect to a given labeled terminator. Furthermore, in a related grammatical construction, a given unlabeled terminator may be said to "correspond" to a given labeled terminator; conversely, a given labeled terminator may be said to "correspond" to a given unlabeled terminator. A labeled terminator and corresponding unlabeled terminator may have different nucleotide bases. For example, a labeled terminator may have thymine as a base and a corresponding unlabeled terminator may have uracil. In a preferred embodiment of the invention, the nucleotide base of the corresponding unlabeled terminator is the same as the nucleotide base of the labeled terminator to which the unlabeled terminator corresponds. For example, ddGTP (guanine triphosphate) labeled with a rhodamine dye attached to the base serves to define dGTP as a corresponding unlabeled terminator. A labeled terminator and corresponding unlabeled terminator may have the same or different mechanisms for effecting the termination of chain extension. For example, the labeled terminator may have a fluorine at the 3' position of the ribose voice the of the nucleotide and the corresponding unlabeled terminator may have a hydrogen at the 3' position of the ribose moiety. In preferred embodiments of the invention, a corresponding unlabeled terminator does not have a detectable label, e.g., a fluorescent dye. However, a corresponding unlabeled terminator may have a label such as a fluorescent dye, provided that the label does not produce a signal that significantly interferes with the detection of the detectable label on the labeled terminator to which it corresponds (or interferes with the detectable labels present on other labeled terminators present in the reaction mixture).

"Extendable polynucleotide" as used herein refers to a polynucleotide or polynucleotide analogs that have a free 3'-OH (or functional equivalent thereof) that can be extended by at least one nucleotide triphosphate in a chain extension reaction catalyzed by a DNA polymerase. The term extendable polynucleotides include both naturally synthesized polynucleotides and synthesized oligonucleotides. Extendable polynucleotides may be of virtually any length, provided they are sufficiently long to hybridize to a polynucleotide of interest in the environment in which claim extension in to take place. Typically, although no necessarily, extendable polynucleotides are at least 14 bases in length.

"Spectrally Resolvable": means, in reference to a set of fluorescent dyes, that the fluorescence emission bands of the respective dyes are sufficiently distinct, i.e., sufficiently non-overlapping, that the dyes, either alone or when conjugated to other molecules or substances, are distinguishable from one another on the basis of their fluorescence signals using standard photodetection systems such as photodetectors employing a series of band pass filters and photomultiplier tubes, charged-coupled devices (CCD), spectrographs, etc., as exemplified by the systems described in U.S. Pat. Nos. 4,230,558 and 4,811,218 or in Wheeless et al., 1985, *Flow Cytometry: Instrumentation and Data Analysis*, pp. 21–76, Academic Press, New York. Preferably, all of the dyes comprising a spectrally resolvable set of dyes are excitable by a single light source.

"Nucleotide base": and "Nucleoleobase": refer to a substituted or unsubstituted nitrogen-containing parent heteroaromatic ring of a type that is commonly found in nucleic acids. Typically, but not necessarily, the nucleobase is capable of forming Watson-Crick and/or Hoogsteen hydrogen bonds with an appropriately complementary nucleobase. Exemplary nucleobases include, but are not limited to, purines such as 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG) hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. Additional exemplary nucleobases can be found in Fasman, 1989, *Practical Handbook of Biochemistry and Molecular Biology*, pp. 385–394, CRC Press, Boca Raton, Fla., and the references cited therein. Preferred nucleobases are purines, 7-deazapurines and pyrimidines. Particularly preferred nucleobases are the normal nucleobases, defined infra, and their common analogs, e.g., 2ms6iA, 6iA, 7-deaza-A, D, 2dmG, 7-deaza-G, 7mG, hypoxanthine, 4sT, 4sU and Y.

"Normal Nucleobase": refers to a nucleobase that is naturally-occurring and encoding, i.e., adenine, cytosine, guanine, thymine or uracil.

"Nucleoside": refers to a compound consisting of a nucleobase covalently linked, typically via a heteroaromatic ring nitrogen, to the C-1' carbon of a pentose sugar. Typical pentose sugars include, but are not limited to, those pentoses in which one or more of the carbon atoms are each independently substituted with one or more of the same or different —R, —OR, —NRR or halogen groups, where each R is independently hydrogen, $(C_1-C_6)$ alkyl or $(C_5-C_{14})$ aryl. The pentose sugar may be saturated or unsaturated. Exemplary pentose sugars include, but are not limited to, ribose, 2'-deoxyribose, 2'-$(C_1-C_6)$alkoxyribose, 2'-$(C_5-C_{14})$ aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-$(C_1-C_6)$alkylribose, 2'-deoxy-3'-$(C_1-C_6)$alkoxyribose and 2'-deoxy-3'-$(C_5-C_{14})$aryloxyribose.

When the nucleobase is a purine or a 7-deazapurine, the pentose sugar is attached to the $N^9$-position of the nucleobase. When the nucleobase is a pyrimidine, the pentose sugar is attached to the $N^1$-position of the nucleobase (see, e.g., Komberg and Baker, 1992, *DNA Replication, $2^{nd}$ Ed.*, Freeman, San Francisco), except for pseudouridines, in which the pentose sugar is attached to the $C^5$ position of the uracil nucleobase. Preferred nucleosides are those in which the nucleobase is a purine, a 7-deazapurine, a pyrimidine, a normal nucleobase or a common analog of a normal nucleobase and the pentose sugar is any of the exemplary pentose sugars listed above.

"Nucleotide": refers to a nucleoside in which one or more, typically one, of the pentose carbons is substituted with a phosphate ester having the formula:

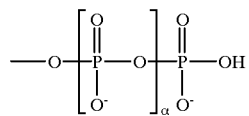

where α is an integer from 0 to 4. Preferably, a is 2 and the phosphate ester is attached to the 3'- or 5'-carbon of the pentose. Particularly preferred nucleotides are those in which the nucleobase is a purine, a 7-deazapurine, a pyrimidine, a normal nucleobase or a common analog thereof.

"Nucleotide Analog": refers to a nucleotide in which the pentose sugar and/or one or more of the phosphate esters is replaced with its respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present.

Also included within the defintion of "nucleotide analog" are nucleobase monomers which can be polymerized into polynucleotide analogs in which the DNA/RNA phosphate ester and/or sugar phosphate ester backbone is replaced with a different type of linkage.

"Enzymatically-Incorporable Nucleotide or Nucleotide Analog": refers to a nucleotide or nucleotide analog which is capable of acting as a substrate for a polymerizing enzyme in a template-directed nucleic acid synthesis reaction such that it is enzymatically incorporated into a nascent polynucleotide or polynucleotide analog chain. Typical enzymatically-incorporable nucleotides and nucleotide analogs are those in which the sugar is a pentose. Preferred enzymatically-incorporable nucleotides are those in which the nucleobase is a purine, a 7-deazapurine, a pyrimidine, a normal nucleobase or a common analog thereof and the pentose is a pentose-5'-triphosphate, such as NTPs, dNTPs and ddNTPs.

"Enzymatically-Extendable Nucleotide or Nucleotide Analog": refers to an enzymatically-incorporable nucleotide or nucleotide analog that, once incorporated into the nascent polynucleotide or polynucleotide analog chain, supports incorporation of further nucleotides or nucleotide analogs. Thus, enzymatically-extendable nucleotides or nucleotide analogs have a hydroxyl group that is capable of forming a covalent linkage with another, subsequent nucleotide or nucleotide analog. Typical enzymatically-extendable nucleotides and nucleotide analogs are those in which the sugar is a pentose. Preferred enzymatically-extendable nucleotides are those in which the nucleobase is a purine, a 7-deazapurine, a pyrimidine, a normal nucleobase or a common analog thereof and the pentose sugar is a 3'-hydroxylpentose-5'-triphosphate, such as NTPs and dNTPs.

"Polynucleotide": refers to a linear polymeric chain of nucleoside monomer units that are covalently connected to one another by phosphate ester internucleoside linkages. Unless stated otherwise, "polynucleotide" as used herein includes polymers of any length, including oligonucleotides, polynucleotides and nucleic acids as those terms are commonly used in the art. Where polynucleotides of specific size ranges are intended, the number of monomer units is specifically delineated. Thus, polynucleotides according to the invention can range in size from a few monomer units (e.g., 4 to 40), to several hundreds of monomer units, to several thousands of monomer units, or even more monomer units. Whenever a polynucleotide is represented by a sequence of letters, e.g., "ATGCCTG," it will be understood that the sequence is presented in the 5'→3' direction. 2'-Deoxyribopolynucleotides are preceded with the letter "d", e.g., "d(ATGCCTG)."

Polynucleotides may be composed of a single type of sugar moiety, as in the case of RNA and DNA, or mixtures of different sugar moieties, as in the case of RNA/DNA chimeras. Preferred polynucleotides are ribopolynucleotides and 2'-deoxyribopolynucleotides according to the structural formulae below:

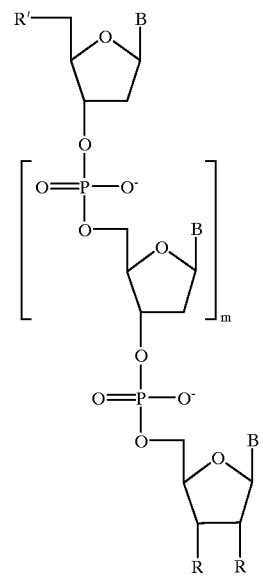

-continued

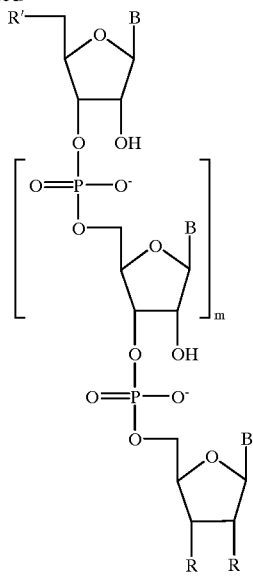

wherein:
  each B is independently a nucleobase, preferably a purine, a 7-deazapurine, a pyrimidine, a normal nucleobase or a common analog thereof;
  each m defines the length of the respective polynucleotide and can range from zero to thousands, tens of thousands, or even more;
  each R is independently selected from the group consisting of hydrogen, halogen, —R", —OR", and —NR"R", where each R" is independently ($C_1$–$C_6$) alkyl or ($C_5$–$C_{14}$) aryl, or two adjacent Rs are taken together to form a bond such that the ribose sugar is 2',3'-didehydroribose; and
  each R' is independently hydroxyl or

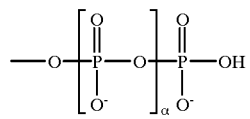

where a is zero, one or two.

In the preferred ribopolynucleotides and 2'-deoxyribopolynucleotides illustrated above, the nucleobases B are covalently attached to the C1' carbon of the sugar moiety as previously described.

"Polynucleotide Analog:" refers to a polynucleotide in which at least one nucleoside monomer unit is a nucleoside analog and/or at least one phosphate ester internucleoside linkage is a phosphate ester analog, as previously defined. Also included within the definition of polynucleotide analogs are polynucleotides in which the phosphate ester and/or sugar phosphate ester internucleoside linkages are replaced with other types of linkages, such as N-(2-aminoethyl)-glycine amides and other amides (see, e.g., Nielsen et al., 1991, Science 254:1497–1500; WO 92/20702; U.S. Pat. No. 5,719,262; U.S. Pat. No. 5,698,685;); morpholinos (see U.S. Pat. No. 5,698,685; U.S. Pat. No. 5,378,841; U.S. Pat. No. 5,185,144); carbamates (see Stirchak & Summerton, 1987, J. Org. Chem. 52:4202); methylene(methylimino) (see Vasseur et al., 1992, J. Am. Chem. Soc. 114:4006); 3'-thioformacetals (see Jones et al., 1993, J. Org. Chem. 58:2983); sulfamates (see U.S. Pat. No. 5,470,967); and others (see, e.g., U.S. Pat. No. 5,817,781; Frier & Altman, 1997, Nucl. Acids Res. 25:4429 and the references cited therein).

EMBODIMENTS OF THE INVENTION

The invention relates to improved methods and assays for identifying a nucleotide base at a predetermined location on a polynucleotide of interest. A nucleotide base is identified by incorporating a labeled terminator that base pairs with the nucleotide base having identity to be determined. A detectable label on the incorporated terminator indicates the identity of the nucleotide base to be determined. The improvement relates to the use of one or more unlabeled terminators that correspond to the labeled terminators to be incorporated into an extendable polynucleotide (e.g., a primer). By employing corresponding unlabeled terminators in DNA polymerization reactions, variations among the incorporation biases against different labeled terminators may be modulated, thereby permitting the equalization of signal strength without significantly increasing misincorporation of labeled terminators. One embodiment of the invention relates to an improvement of the technique commonly known as mini-sequencing (see Syvanen et al, Genomics 8, 684–642 (1990). U.S. Pat. No. 5,888,819, Euoropean patent application EP 0648280 A1).

The subject methods and assays include the step of forming a duplex (double stranded polynucleotide) between a polynucleotide molecule for analysis and an extendable polynucleotide. The extendable polynucleotide hybridizes to a predetermined location on the polynucleotide for analysis such that in the 3' terminus of the extendable polynucleotide hybridizes to a nucleotide base on the polynucleotide for analysis that is located immediately adjacent and 3' to the nucleotide base at the location for analysis, thereby forcing the next nucleotide to be incorporated into the extendable polynucleotide to base pair with nucleotide base to be identified. In many embodiments of the invention, the extendable polynucleotide is an oligonucleotide primer and the polynucleotide molecule for analysis is from a genomic or cDNA preparation. The step of duplex formation may take place by polynucleotide hybridization or may take place concomitantly with a reaction that generates a duplex polynucleotide. For example, a duplex between an extendable polynucleotide and a polynucleotide for analysis may be formed during the process of a restriction endonuclease digestion, e.g., the recessed 3' end of the digestion product can serve as the polynucleotide for extension. The extendable polynucleotide may or may not be perfectly complementary to the polynucleotide for analysis. Thus, the duplex may contain one or more mismatches, provided that the mismatches do not significantly interfere with the ability of a DNA polymerase to extend the extendable polynucleotide or interfere with the ability of the 3' terminus nucleotide base of the extendable polynucleotide to hybridize immediately adjacent to a predetermined location on the polynucleotide for analysis.

The polynucleotide for analysis serves as a template for the labeled terminators that are incorporated into the extendable polynucleotide. The polynucleotide for analysis may be produced by any of a variety of polynucleotide preparation techniques generally known to those of ordinary skill in the art of molecular biology. Examples of such preparation techniques include, direct extraction of polynucleotides, cDNA formation, nucleic acid amplification (e.g., the polymerase chain reaction), and the like.

Subsequent to the formation of the hybrid polynucleotide molecule, the extendable polynucleotide is extended by one nucleotide base in a DNA polymerase catalyzed polynucleotide chain extension reaction. The single incorporated nucleotide base is complementary to the nucleotide base to be determined. The extension reaction takes place in a reaction extension mixture comprising a first labeled terminator, a second labeled terminator and a first unlabeled terminator that corresponds to either the first or second labeled terminators. The extension reaction mixture also comprises other reagents necessary for primer extension such as a DNA polymerase, a buffer suitable for the DNA polymerase, and the like. The extension may take place in the presence of additional labeled terminators and corresponding unlabeled terminators. In preferred embodiments of the invention, a corresponding unlabeled terminator is present for all but one of the labeled terminators in the reaction. The different labeled terminators in the reaction mixture are labeled with different labels that are selected so as to not significantly interfere with the detection of the other labels. In preferred embodiments of the invention, the detectable label are fluorescent dyes that are spectrally resolvable from one another. As naturally occurring polynucleotides have one of four possible nucleotide base is at a given position, a set of four labeled terminators is sufficient to determine the identity of a nucleotide base at a given location on a polynucleotide interest. Less than four unlabeled terminators may be employed when the nucleotide base at the predetermined location is known, a priori, not to be of a certain base, thereby obviating the need to test for the presence of that nucleotide base. Examples of different combinations of labeled terminators and corresponding unlabeled terminators include, but are not limited to:

(1) a first labeled terminator, a second labeled terminator, and an unlabeled terminator corresponding to the first labeled terminator, (2) a first labeled terminator, a second labeled terminator, and unlabeled terminators corresponding to the first and second labeled terminators, (3) a first labeled terminator, a second labeled terminator, a third labeled terminator, and unlabeled terminator corresponding to the first labeled terminator, (4) a first labeled terminator, a second labeled terminator, a third labeled terminator, and unlabeled terminators corresponding to the first and second labeled terminators, (5) a first labeled terminator, a second labeled terminator, a third labeled terminator, and unlabeled terminators corresponding to the first, second and third labeled terminators, (6) a first labeled terminator, a second labeled terminator, a third labeled terminator, and a fourth labeled terminator, and unlabeled terminators corresponding to the first labeled terminators, (7) a first labeled terminator, a second labeled terminator, a third labeled terminator, and a fourth labeled terminator, and unlabeled terminators corresponding to the first and second labeled terminators, (8) a first labeled terminator, a second labeled terminator, a third labeled terminator, and a fourth labeled terminator, and unlabeled terminators corresponding to the first, second, and third labeled terminators, and (9) a first labeled terminator, a second labeled terminator, a third labeled terminator, and a fourth labeled terminator, and unlabeled terminators corresponding to the first, second, third, and fourth labeled terminators.

The different labeled terminators present in a reaction mixture are labeled with different detectable labels that may readily be distinguished from one another. The label on a given labeled terminator is correlated with the chemical structure of the nucleotide base of the terminator. Thus by detecting and identifying the label, the identity of the base may be ascertained. Preferred labels are fluorescent dyes. Preferably, fluorescent dyes are selected for compatibility with detection on an automated DNA sequencer and thus should be spectrally resolvable and not significantly interfere with electrophoretic analysis. In general, fluorescent dye labeled terminators suitable for DNA sequencing by the subject methods are suitable for use in the subject methods. Examples of suitable fluorescent dyes for use as detectable labels on labeled terminators can be found in among other places, U.S. Pat. No. 5,750,409; U.S. Pat. No. 5,366,860; U.S. Pat. No. 5,231,191; U.S. Pat. No. 5,840,999; U.S. Pat. No. 5,847,162; U.S. application Ser. No. 09/038,191, filed Mar. 10, 1998; U.S. application Ser. No. 09/277,793, filed Mar. 27, 1999; PCT Publication WO 97/36960; PCT Publication WO 99/27020; Sauer et al, 1995, J. Fluorescence 5(3):247–261; Arden-Jacob, 1993, *Neue Lanwellige Xanthen-Farbstoffe für Fluoreszenzsonden und Farbstoff Laser,* Verlag Shaker, Germany; Lee et al., 1992, Nucl. Acids Res. 20(10):2471–2483, U.S. Pat. No. 4,439,356; U.S. Pat. No. 4,481,136; U.S. Pat. No. 5,188,934; U.S. Pat. No. 5,654,442; U.S. Pat. No. 5,840,999; WO 99/16832; EP 0 050 684, U.S. Pat. No. 5,750,409 and U.S. Pat. No. 5,066,580, U.S. Pat. No. 5,750,409; U.S. Pat. No. 5,366,860; U.S. Pat. No. 5,231,191; U.S. Pat. No. 5,840,999; U.S. Pat. No. 5,847,162; U.S. application Ser. No. 09/038,191, filed Mar. 10, 1998; U.S. application Ser. No. 09/277,793, filed Mar. 27, 1999; U.S. application Ser. No. 09/325,243, filed Jun. 3, 1999; PCT Publication WO 97/36960; PCT Publication WO 99/27020; Sauer et al., 1995, J. Fluorescence 5(3):247–261; U.S. Pat. No. 5,750,409; U.S. Pat. No. 5,066,580; U.S. Pat. No. 4,439,356; U.S. Pat. No. 4,481,136; U.S. Pat. No. 5,188,934; U.S. Pat. No. 5,654,442; U.S. Pat. No. 5,840,999; PCT publication WO 99/16832; EP 0 050 684, U.S. Pat. No. 5,486,616; U.S. Pat. No. 5,569,587; U.S. Pat. No. 5,569,766; U.S. Pat. No. 5,627;027; U.S. Pat. No. 5,321,130; U.S. Pat. No. 5,410,030; U.S. Pat. No. 5,436,134; U.S. Pat. No. 5,534,416; U.S. Pat. No. 5,582,977; U.S. Pat. No. 5,658,751; U.S. Pat. No. 5,656,449; U.S. Pat. No. 5,863,753; and Tu et al., 1998, Nucl. Acids Res. 26(11):2797–2802. An example of a set of four fluorescent dyes for use as detectable labels with four labeled terminators to be used in conjunction with one another is (1) TAMPA (tetramethyl rhodamine), (2) R6G (rhodamine 6G), (3) R110 (rhodamine 110), and (4) RROX (rhodamine X).

The polynucleotide extension reactions employed in the subject methods are catalyzed by a DNA polymerase. A wide variety of DNA polymerases maybe used in the subject methods. Suitable DNA polymerases for use in the subject methods may or may not be thermostable. DNA polymerases having mutations that reduce discrimination against the incorporation of chain terminators that are 3'-dideoxynucleotides as compared with nucleotide triphosphates are preferred. Particularly preferred is the use of mutants having a Tyr residue at position 667 (numbered with reference to Taq DNA polymerase). A detailed description of such mutants can be found in U.S. Pat. No. 5,614,365. Such mutant polymerases may conveniently be referred to collectively as Y667 mutants.

After the polynucleotide extension reaction has been performed, the extension products are analyzed so as to identify the detectable label that has become incorporated into the extendable polynucleotide through a labeled terminator. Suitable apparatus for detecting the detectable label will vary in accordance with the nature of the particular label employed in the given embodiment. For example, a fluorescent label may be identified with a fluorescence detection system; a radioactive label may be identified with a radiation detection system. Most detection methods suitable for detecting and analyzing labeled terminator incorporation in DNA sequencing (for example as described in U.S. Pat. No. 5,821,058 or U.S. Pat. No. 4,811,218) may be used to detect the incorporation of labeled terminators in the subject methods.

In preferred embodiments of the invention, the primer extension products labeled terminators are separated from the polynucleotide for analysis prior to or concurrent with the incorporation of the detectable label. Such separation may be achieved in a variety of ways, including, but not limited to, electrophoresis, separation of extended primers by binding to a solid phase via a binding moiety on the extendable primer, separation of the extended primers by binding a solid phase in a binding moiety on the labeled terminator, chromatography, and the like. Suitable electrophoretic detection and separation systems include systems designed for the simultaneous electrophoretic separation and detection of fluorescently labeled polynucleotides, e.g., automated DNA sequencers such as the PE Applied Biosystems (Foster City, Calif., USA) 310, 377, or 3700.

In many embodiments of the subject methods,. particularly those embodiments of the invention that employ electrophoretic separation, it is preferable to reduce or remove background signals produced by the detectable label on unincorporated labeled terminators. It is desirable to remove the unincorporated labeled terminators because the signal from the detectable label on the unincorporated terminators may interfere with the detection of signal generated from the label incorporated during primer extension. The unincorporated labeled terminators may be removed by a variety of different methods. The operability of the subject methods is not dependent upon the precise method of removal. One embodiment of such removal methods is the adsorption of the unincorporated terminators, such as by QIAquick™ PCR purification kit spin column (Qiagen, Venlo, Netherlands). In a preferred embodiment of the invention, the unincorporated labeled terminators are separated on the basis of differential electrophoretic migration by altering the electrophoretic mobility properties of the unincorporated terminators. The electrophoretic mobility of the unincorporated labeled terminators may be altered by treating the terminators with an alkaline phosphatase, shrimp alkaline phosphatase being particular preferred.

The subject methods are generally performed in the absence of significant amounts of nucleotide triphosphates that are not terminators, i.e., do not produce extendable 3' ends upon incorporation into the extendable polynucleotide, e.g., dATP. By absence of significant amounts, is intended that there be insufficient quantities of extendable terminators present so as to produce amounts of labeled primer extension products that are extended by more than one nucleotide base (detectable via the means used to detect of the detectable label) in sufficient quantity to produce a detectable signal that could interfere with the interpretation of the signal from extendable polynucleotides that have incorporated only a single nucleotide.

The ratio of a labeled terminator to corresponding unlabeled terminator present in a reaction mixture may vary. Useful ratios of terminators and corresponding unlabeled terminators will vary in accordance with the structures of labeled terminators and corresponding unlabeled terminators used in a given embodiment of the invention. Useful ratios of terminators will also vary in accordance with the specific DNA polymerase used. Generally the ratio will be selected so as to produce similar or equivalent signal detectable label signal strengths from the different labeled terminators in a given reaction mixture. By use of the term "similar", it is intended that the signal strength produced by different labeled terminators upon incorporation (in essentially the same assay format) vary between each other by no more than 25%, preferably by less than 15%, more preferably by less than 10%, and even more preferably by less than 5%. By adding corresponding unlabeled terminators, the signal strength produced by a reaction with a given labeled terminator may be decreased. The invention includes sets of labeled terminators and corresponding unlabeled terminators that produce similar or equivalent detectable label signal strengths upon incorporation; such sets may be conveniently referred to as "matched sets" of labeled terminators and corresponding unlabeled terminators. The use of matched sets to produce equivalent or similar signal strengths is of particular interest when analyzing a mixed population of polynucleotide targets, such as SNP detection in heterozygotes. By controlling for differences in signal strength caused by selective incorporation, heterozygotes (that result in the production of composite signals) may readily be distinguished from misincorporation background. An example of a matched set of four fluorescent dye labeled terminators (in a 10 $\mu$l volume) is a mixture comprising 0.5 pmol ddATP-R6G, 0.42 pmol ddATP, 4.0 pmol ddCTP-Tamra, 3.2 pmol ddCTP, 0.6 pmol ddGTP-R110, 0.6 pmol ddGTP, and 6.0 pmol ddUTP-RROX.

The ratios and concentrations of labeled terminators and corresponding unlabeled terminators required to produce a matched set of labeled terminators and corresponding unlabeled terminators may be determined empirically. An example of how to make such an empirical determination is given as follows. Multiple assays for measuring the incorporation of labeled terminators are prepared. Each assay is essentially the same, but differs with respect to the identity of the nucleotide base incorporated. Exemplary assays have a primer (i.e., an extendable polynucleotide), template (i.e., a polynucleotide for analysis), a DNA, polymerase, a buffer suitable for the DNA polymerase, and the labeled terminator of interest. A set of labeled terminators (at least two labeled terminators in the set) is selected. Each labeled terminator in the set is then assayed in a polynucleotide extension assay specific for the nucleotide base of interest. The labeled terminators set member that generates the lowest signal strength is then determined and used as the standard against which the assays signal strength produced by other labeled terminators in the set is modulated. Alternatively, the standard may be set using a mixture of labeled terminator and corresponding unlabeled terminators. The strength of the signal from assays employing the other labeled terminators in the set can be modulated by performing titrations in which the assays is performed repeatedly under the same reaction conditions, but using increasing amounts of a corresponding unlabeled terminator. The titration assays may be used to determine the amount of corresponding unlabeled terminator to add so as to attenuate signal strength down to the level similar or identical to the intensity of the signal strength produced by assays employing the labeled terminator selected as the standard. The titration experiments may or may not be carried out using a constant total amount of terminator (i.e., labeled terminator plus corresponding unlabeled terminator).

It will be readily appreciated to those skilled in the art that the subject methods and compositions may readily be "multiplexed" so as to simultaneously perform multiple analyses in a single reaction mixture. Multiplexation may be achieved in embodiments of the subject invention adapted for electrophoretic detection. A plurality of extendable polynucleotides, each hybridized to a different polynucleotide for analysis (or multiple, non-interfering, sites on a larger polynucleotide for analysis), are differentially mobile during electrophoresis for its separation to achieve multiplexation, see, U.S. Pat. No. 5,925,520. Differential mobility may be achieved by varying the sizes of the polynucleotides for extension (primers) or by modifying mobility of the primer by attaching mobility modifying moieties, for example as described in U.S. Pat. No. 5,514,543.

The invention also includes compositions for performing the subject methods of identifying a nucleotide base at a predetermined location on a polynucleotide molecule for analysis. The compositions of the invention include mixtures that are formed in the course of performing the methods of the invention or compositions that may be formed in the process of preparing to perform methods of the invention. Examples of the subject composition include mixtures comprising the combinations of labeled terminators and corresponding unlabled terminators for use in the subject methods as described above with respect to the subject methods, e.g., (I) a first labeled terminator, a second labeled terminator, and an unlabeled terminator corresponding to the first labeled terminator, (ii) a first labeled terminator, a second labeled terminator, a third labeled terminator, and a fourth labeled terminator, and unlabeled terminators corresponding to the first, second, and third labeled terminators, and the like.

Preferably, the compositions are matched sets of terminators and corresponding unlabeled terminators. The subject compositions may also comprise one or more of the following reagents employed in the subject methods: an extendable polynucleotide, a polynucleotide for analysis, and a DNA polymerase.

The invention also includes kits for identifying a nucleotide base at a predetermined location on a polynucleotide of interest. Embodiments of the subject kits include a plurality of reagents that may be used to identify nucleotide bases in accordance with the methods of the invention. Kits of the invention, in addition to the reagents, preferably include written instructions for performing the subject methods. The subject kits comprise two or more labeled terminators and one or more unlabeled terminators. Kits are preferably packaged in a unit container and may contain the reagents in pre-measured amounts designed to operate with each other so as to produce the desired result. The kits contain a labeled terminator and a corresponding unlabeled terminator present in the same solution. The kits of the invention may also include additional labeled terminators and corresponding unlabeled terminators present in the same solution or in separate solutions. The compositions in the kits comprising labeled terminators and corresponding unlabeled terminators are preferable matched sets. The kits may further comprise one or more of the following items, DNA polymerase, alkaline phosphatase, chromatography columns, reaction buffers, amplification primers, and exonuclease for degrading excess amplification primers.

INCORPORATION BY REFERENCE

All papers and documents (including patents) referenced in this specification are incorporated herein by reference.

EQUIVALENTS

While the invention has been described with reference to specific methods and embodiments, it will be appreciated that various modifications and changes may be made without departing from the invention. These and other equivalents are intended to be covered by the following claims.

What is claimed is:

1. A method of identifying a nucleotide base at a predetermined location on a polynucleotide molecule for analysis, said method comprising, forming a hybrid polynucleotide molecule, said hybrid comprising,
the polynucleotide for analysis,
an extendable polynucleotide having a 3' terminus nucleotide base, wherein the extendable polynucleotide is hybridized to the polynucleotide for analysis, and wherein the 3' terminus nucleotide base is hybridized to nucleotide base on the polynucleotide for analysis that is located 3' adjacent to the nucleotide base at the predetermined location, extending the extendable polynucleotide by one nucleotide base, wherein the extending takes place in a reaction solution comprising,
a first labeled terminator comprising a first nucleotide base and a first detectable label,
a second labeled terminator comprising a second nucleotide base and a second detectable label, and
a first corresponding unlabeled terminator comprising the first nucleotide base.

2. The method according to claim 1, wherein the reaction solution further comprises
a second corresponding unlabeled terminator comprising the second nucleotide base.

3. The method according to claim 2, wherein the reaction solution further comprises
a third labeled terminator comprising a third nucleotide base and a third detectable label.

4. The method according to claim 3, wherein the reaction solution further comprises
a corresponding third unlabeled terminator comprising the third nucleotide base.

5. The method according to claim 4, wherein the reaction solution further comprises
a fourth labeled terminator comprising a fourth nucleotide base and a fourth detectable label.

6. The method according to claim 5, wherein the reaction solution further comprises
a corresponding fourth unlabeled terminator comprising the fourth nucleotide base.

7. The method of claim 1, wherein the detectable labels are fluorescent dyes.

8. The method of claim 1, wherein the extendable polynucleotide is a synthetically produced oligonucleotide.

9. The method of claim 1, wherein the extending is catalyzed by a DNA polymerase having a mutation that increases the rate of ddTNP incorporation.

10. The method of claim 9, wherein the DNA polymerase is Taq DNA polymerase comprising a Y667 mutation.

11. The composition of claim 10, wherein the detectable labels are flourescent dyes.

12. The composition of claim 10, further comprising
an extendable polynucleotide having a 3' terminus nucleotide base,
wherein the extendable polynucleotide is complementary to the polynucleotide for analysis, and wherein the 3' terminus nucleotide base may be hybridized to the nucleotide base on the polynucleotide for analysis that is located 3' adjacent to the nucleotide base at the predetermined location.

13. A composition for the identification of a nucleotide base at a predetermined location on a polynucleotide molecule for analysis, said composition comprising, a first labeled terminator comprising a first nucleotide base and a first detectable label, a second labeled terminator comprising a second nucleotide base and a second detectable label, and a first corresponding unlabeled terminator comprising the first nucleotide base.

14. A composition according to claim 13, wherein the reaction solution further comprises a second corresponding unlabeled terminator comprising the second nucleotide base.

15. The composition according to claim 14, wherein the reaction solution further comprises a third labeled terminator comprising a third nucleotide base and a third detectable label.

16. The composition according to claim 15, wherein the reaction solution further comprises a third corresponding unlabeled terminator comprising the third nucleotide base.

17. The composition according to claim 16, wherein the reaction solution further comprises a fourth labeled terminator comprising a fourth, nucleotide base and a fourth detectable label.

18. The composition according to claim 17, wherein the reaction solution further comprises a fourth corresponding unlabeled terminator comprising the fourth nucleotide base.

19. A kit for the identification of a nucleotide base at a predetermined location on a polynucleotide molecule for analysis, said kit comprising, a first labeled terminator comprising a first nucleotide base and a first detectable label, a second labeled terminator comprising a second nucleotide base and a second detectable label, and a first unlabeled terminator comprising the first nucleotide base.

20. The kit according to claim 19, said kit further comprising a second unlabeled terminator comprising the second nucleotide base.

21. The kit according to claim 20, said kit further comprising a third labeled terminator comprising a third nucleotide base and a third detectable label, a third unlabeled terminator comprising the third nucleotide base, a fourth labeled terminator comprising a fourth nucleotide base and a fourth detectable label, and a fourth unlabeled terminator comprising the fourth nucleotide base.

22. The kit of claim 19, wherein at least 2 of the reagents are present in the same solution.

23. The kit of claim 19, further comprising a DNA polymerase.

* * * * *